(12) United States Patent
Paige et al.

(10) Patent No.: US 7,406,873 B2
(45) Date of Patent: Aug. 5, 2008

(54) ELECTROMAGNETIC ACOUSTIC TRANSDUCER

(75) Inventors: David Paige, Newcastle-upon-Tyne (GB); Robert Andrew Mercel, Northumberland (GB); Ian Sowerby, Northumberland (GB)

(73) Assignee: PII Limited, Tyne and Wear (GB)

( * ) Notice: Subject to any disclaimer, the term of this patent is extended or adjusted under 35 U.S.C. 154(b) by 273 days.

(21) Appl. No.: 10/560,356

(22) PCT Filed: Jun. 18, 2004

(86) PCT No.: PCT/GB2004/002648

§ 371 (c)(1), (2), (4) Date: May 4, 2006

(87) PCT Pub. No.: WO2004/113906

PCT Pub. Date: Dec. 29, 2004

(65) Prior Publication Data

US 2006/0278000 A1    Dec. 14, 2006

(30) Foreign Application Priority Data

Jun. 19, 2003    (GB)    ................ 0314357.5

(51) Int. Cl.
    *G01N 29/24*    (2006.01)
(52) U.S. Cl. .................................... 73/643
(58) Field of Classification Search ............ 73/643
    See application file for complete search history.

(56) References Cited

U.S. PATENT DOCUMENTS

| | | | | |
|---|---|---|---|---|
| 4,149,421 A | * | 4/1979 | Buttcher et al. | 73/643 |
| 4,665,752 A | * | 5/1987 | Huschelrath et al. | 73/643 |
| 5,537,876 A | * | 7/1996 | Davidson et al. | 73/624 |
| 5,684,406 A | * | 11/1997 | MacLauchlan et al. | 324/700 |
| 6,125,706 A | * | 10/2000 | Buttram et al. | 73/643 |
| 6,282,964 B1 | | 9/2001 | Hancock et al. | |
| 6,404,189 B2 | * | 6/2002 | Kwun et al. | 324/220 |
| 6,546,107 B1 | * | 4/2003 | Bohnke | 381/189 |
| 6,766,694 B2 | * | 7/2004 | Hubschen | 73/643 |
| 2003/0159516 A1 | * | 8/2003 | Hubschen | 73/643 |

FOREIGN PATENT DOCUMENTS

| | | |
|---|---|---|
| DE | 36 37 366 | 5/1988 |
| DE | 195 05 571 | 8/1996 |
| EP | 0 556 557 A1 | 8/1993 |
| GB | 2 385 229 A | 8/2003 |

* cited by examiner

*Primary Examiner*—Hezron Williams
*Assistant Examiner*—Rose M Miller
(74) *Attorney, Agent, or Firm*—Stites & Harbison PLLC; Ross F. Hunt, Jr.

(57) ABSTRACT

An electromagnetic acoustic transducer (12, 24) has one or a plurality of magnets for applying a DEC magnetic field to a material (4, 25) under test, and an electrical coil (2, 23) supplied by an alternating current source for, providing an AC magnetic flux within the material under test. A wear plate (16, 26) engages with an slides along the surface of the material under test. The wear plate (16, 26) is of electrically conductive ferromagnetic material and has apertures (17, 31) therein. Thus, both the DC field and the ACT flux can penetrate the material under test and create ultrasonic vibration of that material.

15 Claims, 10 Drawing Sheets

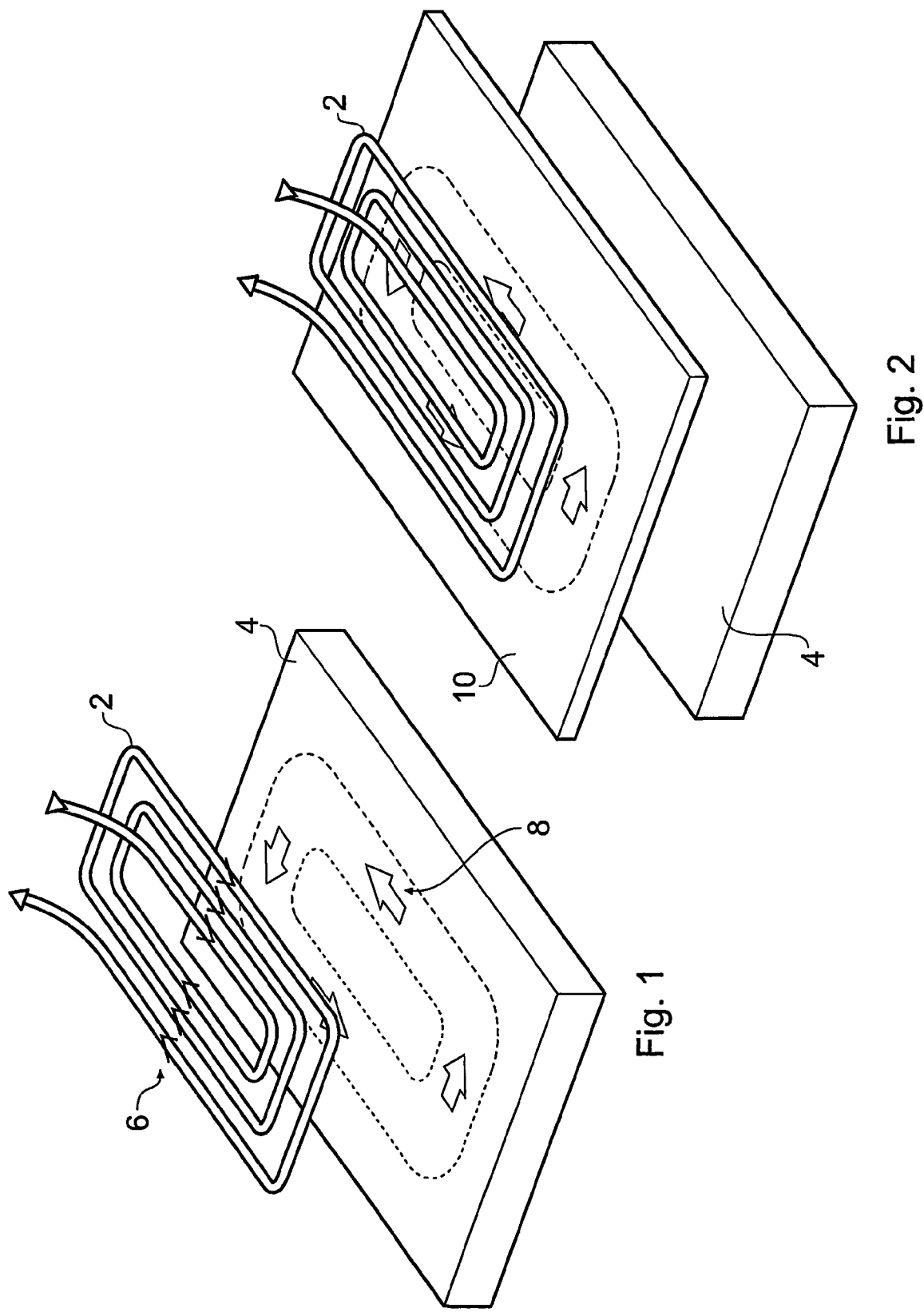

ELECTROMAGNETIC ACOUSTIC TRANSDUCER

BACKGROUND OF THE INVENTION

1. Field of the Invention

This invention relates to electromagnetic acoustic transducers (hereinafter referred to as EMATS) for inspecting the integrity of metallic components, for example pipelines, by ultrasonics.

2. Summary of the Prior Art

Conventional EMATs interact with test materials by the joint action of a steady magnetic field, often produced by one or more permanent magnets, and a transient high frequency magnetic field, produced by an electrical winding. The interaction of the EMAT with the test specimen is usually at A maximum when the gap between the active components of the transducer and the test material is at a minimum.

However, EMATs are subjected to wear if moved while in contact with a test material.

Consequently EMATs to be moved along the surface of a test material require the provision of a protective layer or wear plate between the active components of the EMAT and the surface. This layer is subject to conflicting requirements. Wear resistance improves as layer thickness increases, but the acoustic performance of the EMAT decreases as the layer thickness increases, and is dependent upon the material properties and geometry of the protective layer.

The materials of protective layers usually incorporated in EMATs are chosen to have a negligible interaction with the EMAT, their presence having no other effect on acoustic performance than that associated with introducing an unfilled gap between the active face of the EMAT and the test material. Protective layers made from these materials are typically very thin, because EMAT acoustic performance falls very sharply as the gap increases. Since the material is thin, the lifetime of the wear layer can be short if the abrasion it experiences is particularly severe, for example in long distance high speed inspection of a pipe wall from an internal inspection vehicle or pipeline pig.

The use of electrically conductive and/or ferromagnetic material for the protective plate has heretofore been outlawed because the acoustic performance of the EMAT is severely reduced if a plate of such material is interposed between the EMAT and the material under test.

More particularly the presence of such a plate significantly reduces the penetration of the high frequency magnetic field from the EMAT into the test material due to the electrical skin depth phenomenon, and the DC magnetic field in the test material is reduced due to the removal of D C Flux from the test material by alternative closure paths.

SUMMARY OF THE INVENTION

In view of the excellent wear characteristics of some such materials, it would be desirable if wear plates having electrically conductive and ferromagnetic characteristics could be incorporated into EMATs whilst maintaining an effective acoustic performance from the EMAT.

According to the present invention there is provided an electromagnetic acoustic transducer for exciting ultrasound in a material under test, the transducer comprising magnetic means for applying a DC magnetic field to the material under test, an electrical coil supplied by an alternating current source for providing an AC magnetic flux within the material under test, and a wear plate adapted to engage with and slide along the surface of the material under test, characterised in that the wear plate comprises an electrically conductive, ferromagnetic material having apertures therein configured to provide electrical and magnetic discontinuity in the wear plate and to permit penetration of both the DC magnetic field and the AC magnetic flux into the material under test so as to create, by their interaction, ultrasonic vibration of the material under test.

The precise configuration of the apertures in the wear plate is chosen to suit the type of EMAT and to ensure the establishment of the DC magnetic field and the AC magnetic flux in the material under test.

Note that the magnetic means may be one or more permanent magnets or one or more electromagnets.

A wear plate of an electrically conductive, ferromagnetic material of an EMAT according to the invention can be arranged to have a thickness greatly in excess of conventional non-ferromagnetic, non-electrically conductive wear plates whilst still maintaining acoustic efficiency. This increased thickness and wide choice of material properties for the wear plate allows the operating life of the EMAT to be increased above that possible with conventional wear plates.

In some embodiments of the invention, the apertures comprise a plurality of parallel slots in the wear plate. Those slots may each extend substantially perpendicular to the direction of image current flow in the material under test; but other orientations are possible depending on the waves to be generated in the material under test.

In a transducer according to the invention, of which the magnetic means may comprise a plurality of longitudinally aligned magnets adjacent ones of which have opposite poles abutting one another. It is then preferred that the slots are located below the boundaries between adjacent magnets. In such an arrangement, the EMAT and its wear plate generate in the test material horizontally polarised acoustic shear waves in which the motion of the test material is parallel to the test surface and orthogonal to the wave direction. Note that the invention is not limited to such arrangements.

Preferably the thickness of the wear plate is equal to one quarter of the wavelength of the main wave mode excited within the wear plate.

As mentioned above, the magnetic means may comprise a plurality of longitudinally aligned magnets. Alternatively, the magnetic means may comprise at least one magnet, and the electrical coil is positioned between the at least one magnet and the wear plate, e.g. adjacent the wear plate. The coil has a plurality of meanders therein. The coil may then be arranged to line a plane generally parallel to the wear plate. The meanders preferably change the direction of the coil through 180°, so that the coil comprises a plurality of generally straight and approximately parallel sections joined by the meanders. In such an arrangement, the straight sections are aligned with corresponding plurality of parallel slots in the wear plate. Moreover, in such an arrangement it is desirable for the wear plate to have extensions between the slots, so that pairs of straight section of the coil are separated by a corresponding extension.

BRIEF DESCRIPTION OF THE DRAWINGS

By way of example only, embodiments of the invention will be described in greater detail with reference to the accompanying drawings of which:

FIG. 1 shows part of a conventional horizontally polarised shear wave EMAT with no wear plate between an electrical winding and a material under test;

FIG. 2 shows the arrangement of FIG. 1 with an electrically conductive plate interposed between the winding and the material under test;

DETAILED DESCRIPTION

Figure 3:
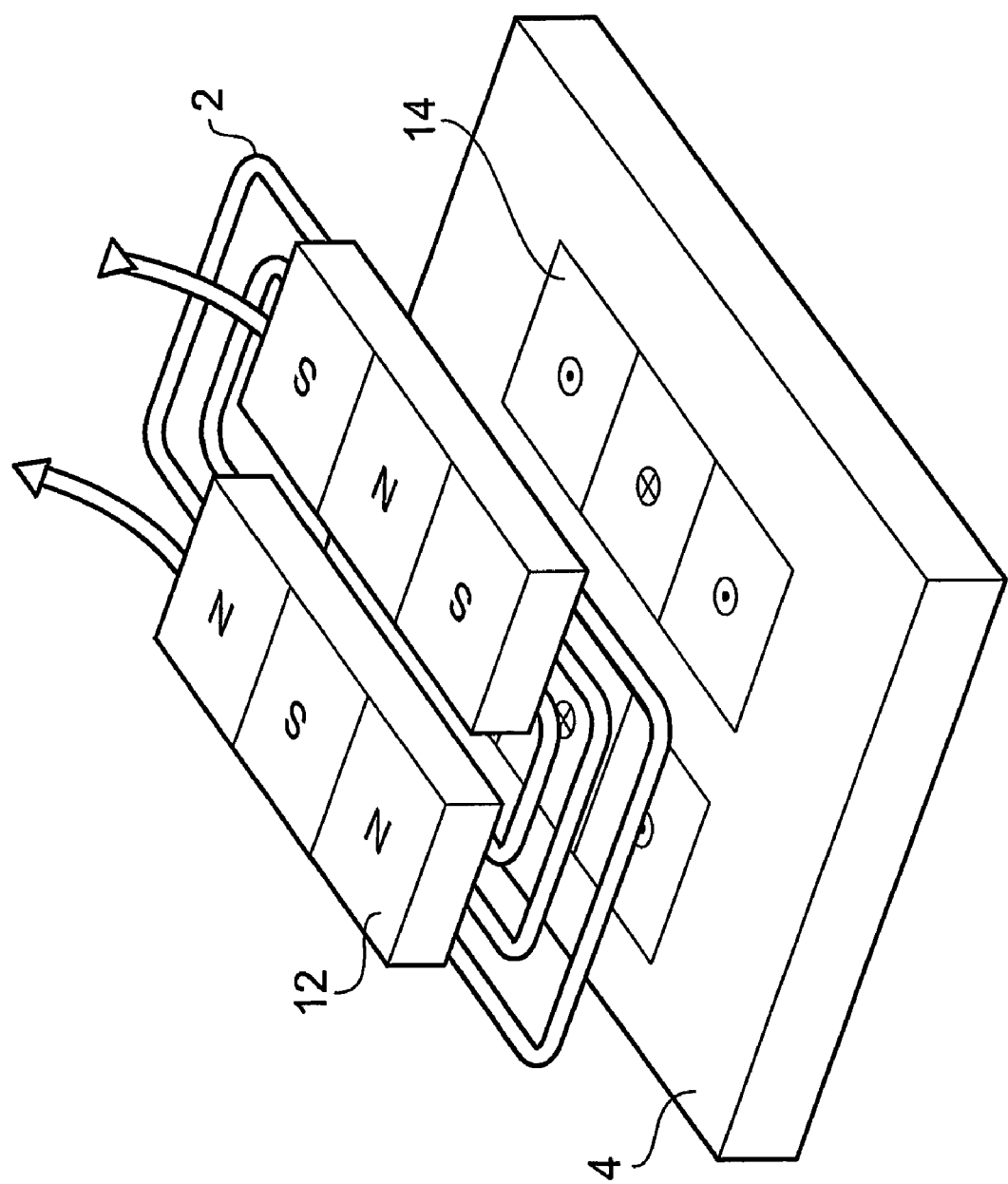
FIG. 3 shows part of a conventional EMAT with magnetic means applying a DC magnetic field to a material under test.

Referring to the drawings, FIG. 1 is an illustration of the AC currents produced by a simple winding such as might typically be used in an EMAT for generating horizontally polarised shear waves. It shows a planar winding 2 above a test sample 4. An AC current passes through the winding and is indicated by current flow arrows 6. These current flows are shown frozen in time, circulating in one arbitrary direction. Image currents 8 are induced into the test sample 4 by the AC winding currents 6 and are in the opposite direction to the AC winding currents 6. They circulate within a plane on the top surface of the test sample 4.

FIG. 2 shows the effect of introducing an electrically conductive plate 10 between the winding 2 and the test sample 4. The image currents 8 now flow in the surface of the conductive plate 10. Unless the conductive plate 10 is very thin or has poor conductivity, it will shield the test sample 4 from the electromagnetic effects of the winding 2 and prevent the circulation of any image currents within the test sample 4. This would prevent the EMAT, which is only partially illustrated in FIG. 2, from functioning.

FIG. 3 shows the DC field pattern in the surface of the test sample 4 created by permanent magnets 12, positioned in a typical arrangement for a horizontally polarised shear wave EMAT. The test sample 4 is shown with areas of differing polarity 14 for the normal magnetic field component in the test sample 4. FIG. 3 shows all the key components of the most commonly used design of horizontally polarised shear wave EMAT.

Figure 4:
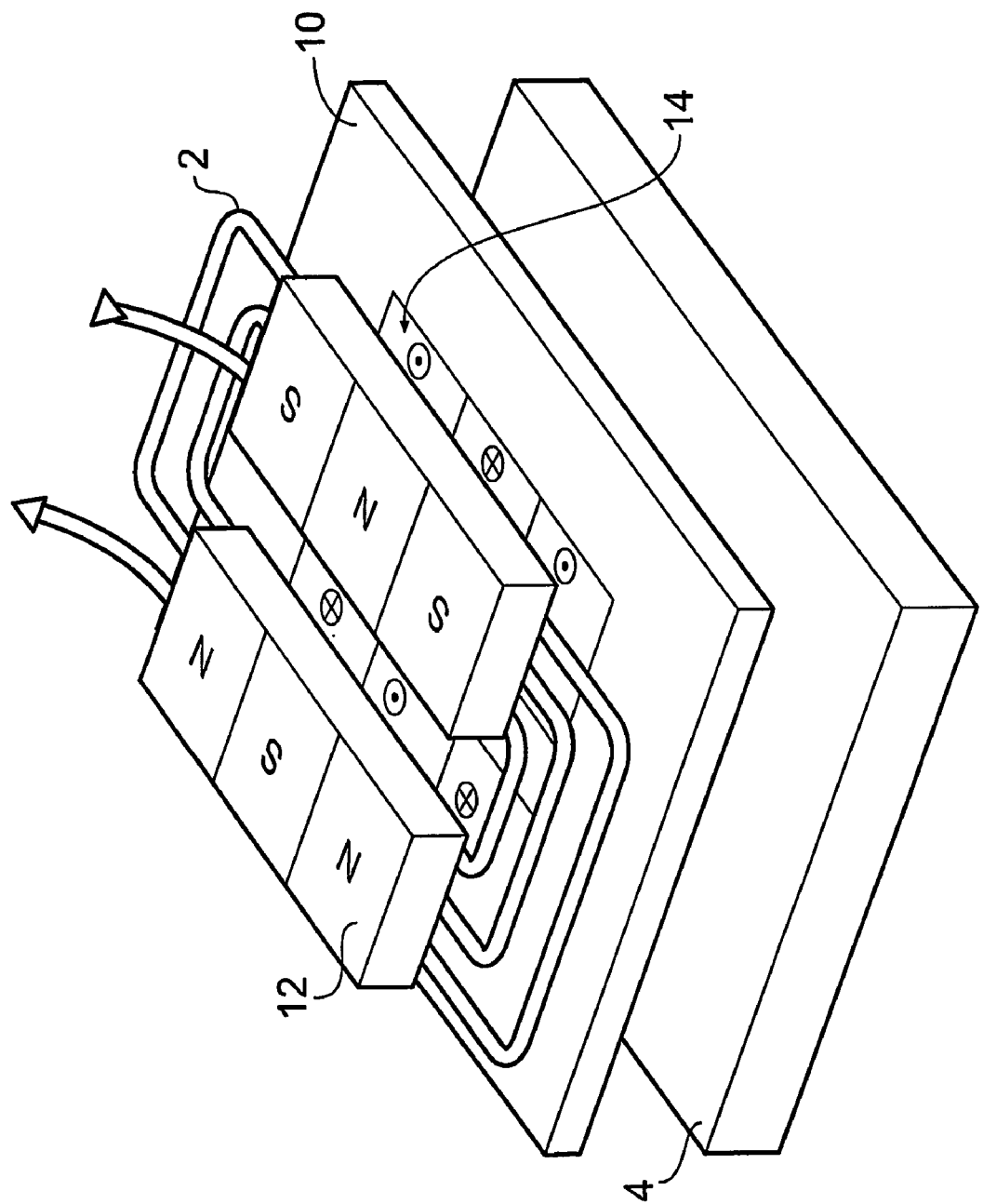
FIG. 4 shows the arrangement of FIG. 3 with an electrically conductive plate interposed between the magnetic means and the material under test.

FIG. 4 shows the effect of introducing an electrically conductive and ferromagnetic plate 10 between the magnets 12 and the test sample 4, the DC magnetic field previously established in the test sample 4 being trapped in the plate 10 and not reaching the test sample 4.

According to the EMAT of the invention, there is provided an electrically conductive ferromagnetic wear plate with apertures therein configured to create electrical and magnetic discontinuity in the wear plate and to permit penetration of both the DC magnetic field and the AC magnetic flux into the material under test so as to create, by their interaction, ultrasonic vibration of the material under test.

Figure 5:
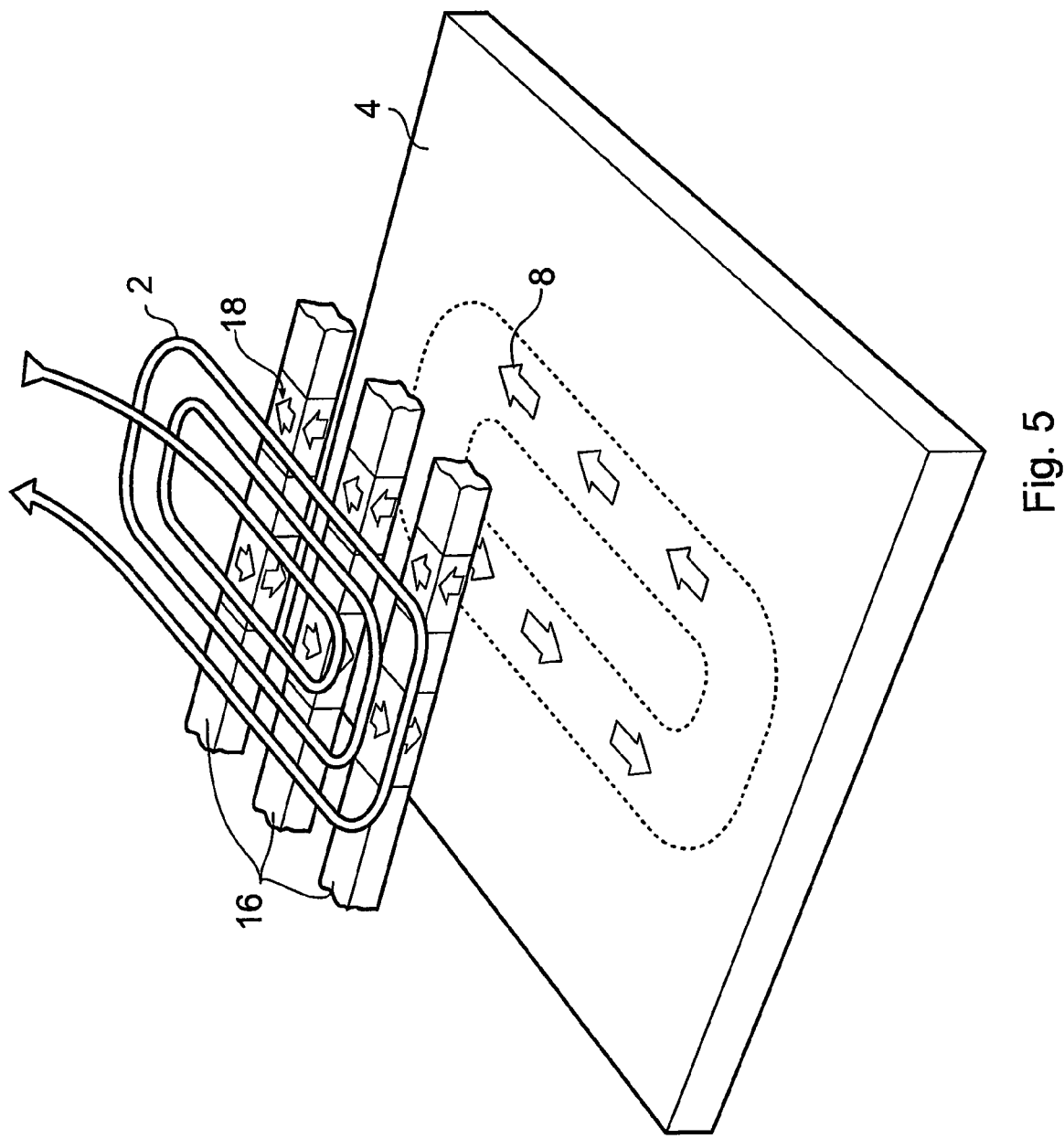
FIGS. 5 and 6 show parts of an EMAT according to an embodiment of the invention.

FIG. 5 shows the effect on the AC current of introducing a slotted electrically conductive plate 16. The plate 16 is shown only in part, namely the region of the slots where the plate 16 appears to be a series of bars, numbering three for the purposes of illustration. The slots are arranged broadly perpendicular to the normal flow of image currents 18 in the conductive plate 16. In this case, image currents flow in both the conductive plate 16 and in the test sample 4, where the direction of flow is similar to the simple case in FIG. 1. In the slotted plate 16, the image currents 18 are forced to travel down the walls of the slots and complete their circuit by travelling along the lower surface of the plate 16 (not visible in FIG. 5) in the opposite direction to the flow on the top surface of the plate 16.

In FIG. 5, the image currents 8 in the test sample 4 can be of higher amplitude than those in FIG. 1, even for an equivalent winding current amplitude and for an equivalent distance between the winding 2 and the test sample 4. This is particularly true when the thickness of the slotted plate 16 occupies a large proportion of the gap between the winding 2 and the test sample 4. For a well designed slotted plate 16, the main contribution to the currents 8 in the test sample 4 are the image currents 18 induced by currents travelling in the slotted plate 16, which in places are physically very close to the test sample 4 and therefore induce strong current flows. The currents 18 in the slotted plate 16 are themselves the image currents from the winding 2, which are induced very strongly into the slotted plate 16 at its top surface where the winding 2 is close to the slotted plate 16. The net effect is that the currents 8 induced in the test sample 4 can be enhanced compared to an arrangement having the same distance between the winding 2 and the test sample 4 but not incorporating a slotted plate 16.

Figure 6:
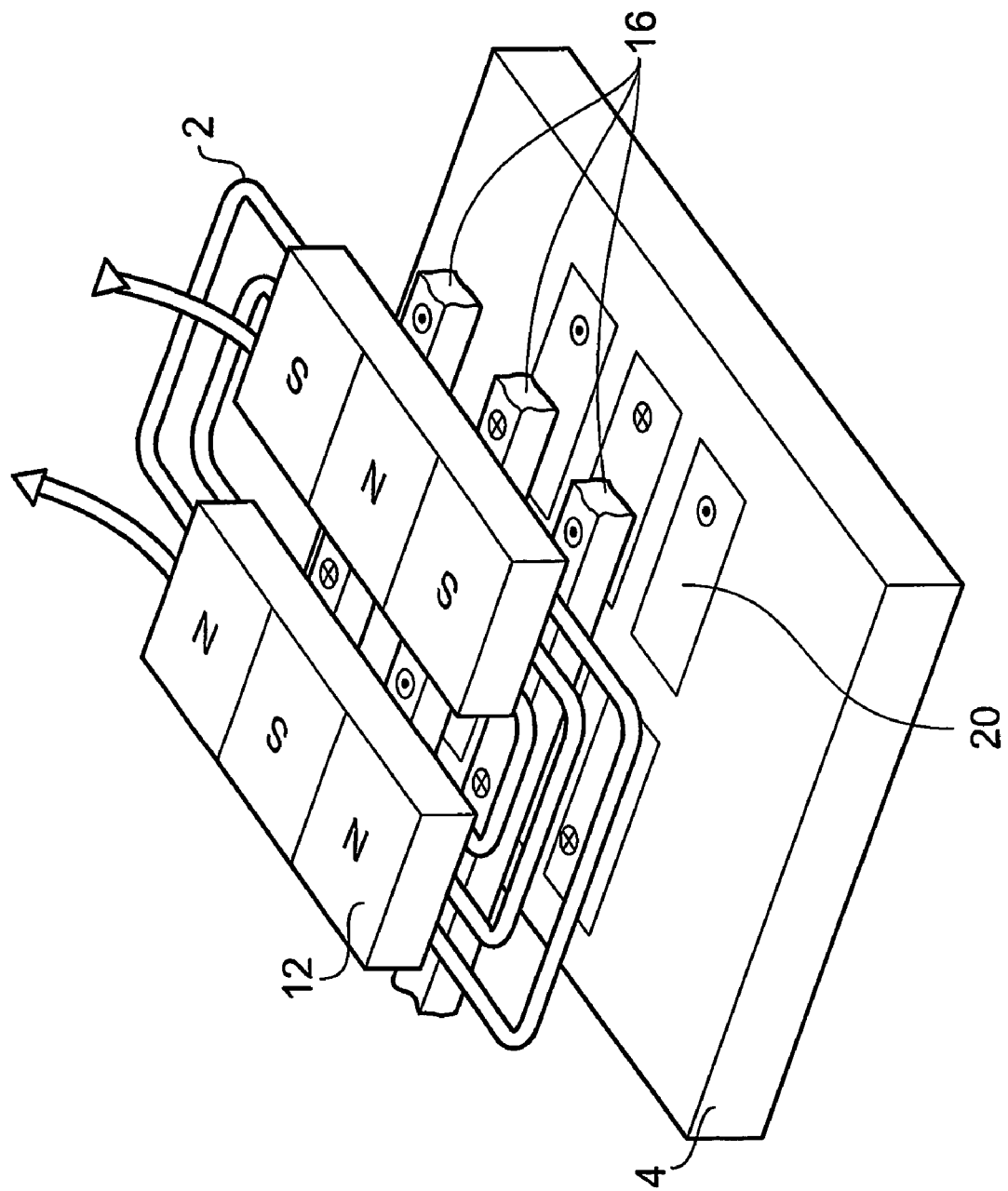

FIG. 6 shows the effect on the DC magnetic field pattern of introducing a ferromagnetic slotted plate 16 between the winding 2 and test sample 4 for the arrangement in FIG. 3. The slotted plate 16 modifies the DC field pattern in the test sample 4, but, by positioning the slots below the boundaries between magnets 12, the field pattern in the test sample 4 is broadly similar to the pattern 14 of FIG. 3. With a well-designed ferromagnetic slotted plate 16, the field intensity in the test sample 4 can be made considerably larger than the field in the absence of the slotted plate 16, for equivalent distance between magnets and test sample.

FIG. 6 shows the key components of a horizontally polarised shear wave EMAT with a slotted wear plate 16. The DC field pattern 20 in the test sample, shown in FIG. 6, and the AC current pattern 8 in the test sample 4, which will be the same as shown in FIG. 5, create the required lorentz forces. The proviso is that the wear plate 16 must be electrically conductive, ferromagnetic and have slots whose geometry enhances both the AC image currents and the DC magnetic fields of the EMAT.

FIGS. 5 and 6 illustrate one particular type of EMAT only, but the principle of using a slotted conductive and ferromagnetic wear plate 16 is applicable to other designs, albeit with different slot arrangements.

Figure 7:
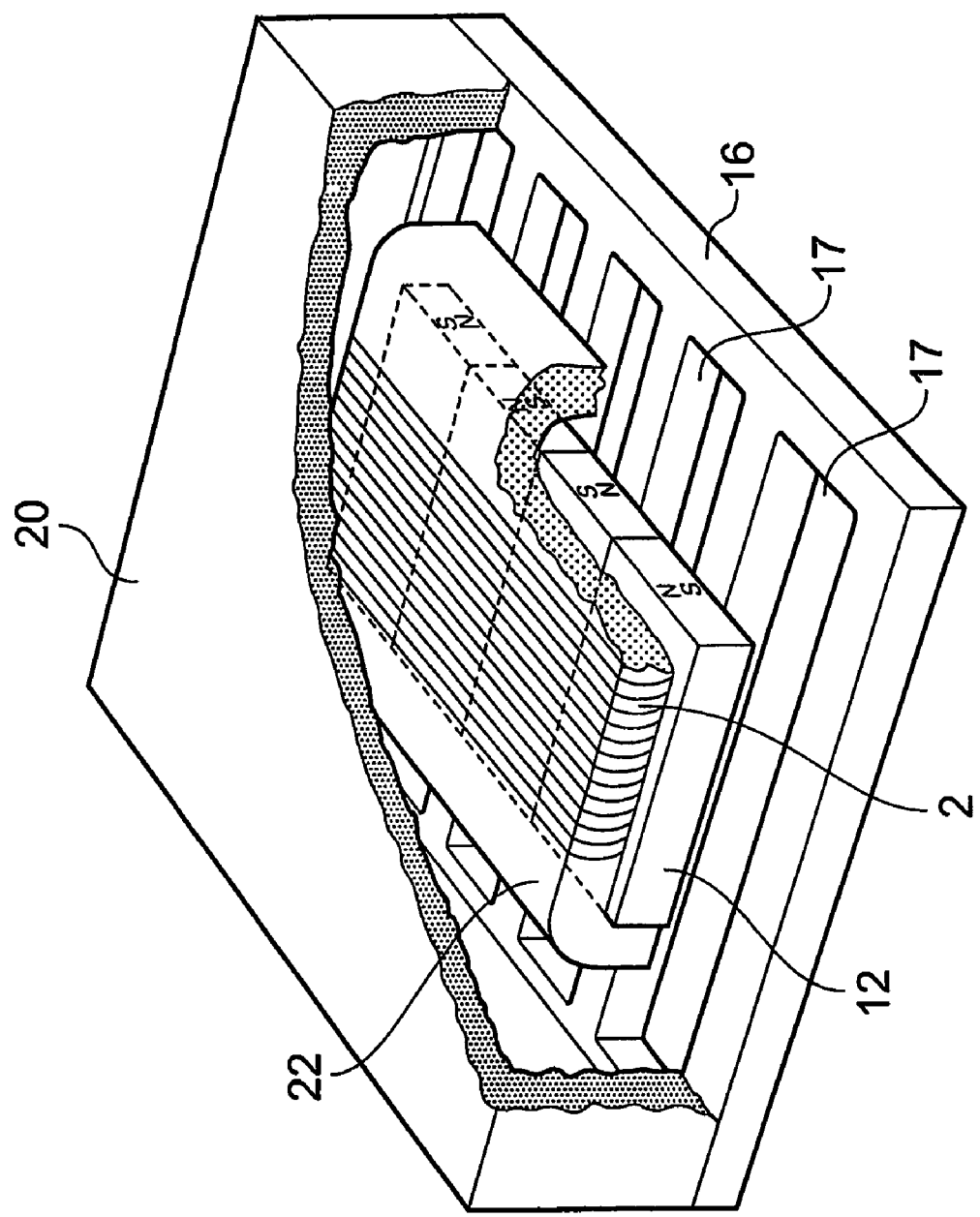
FIG. 7 shows part of one embodiment of the invention.

FIG. 7 shows in more detail part of an EMAT according to the invention. The wear plate 16 with slots 17 is in the form of a grill or grid with the AC winding 2 and the DC magnets 12 contained within a housing 20. The winding 2 comprises a C-core 22 although other configurations may be used.

Figure 8:
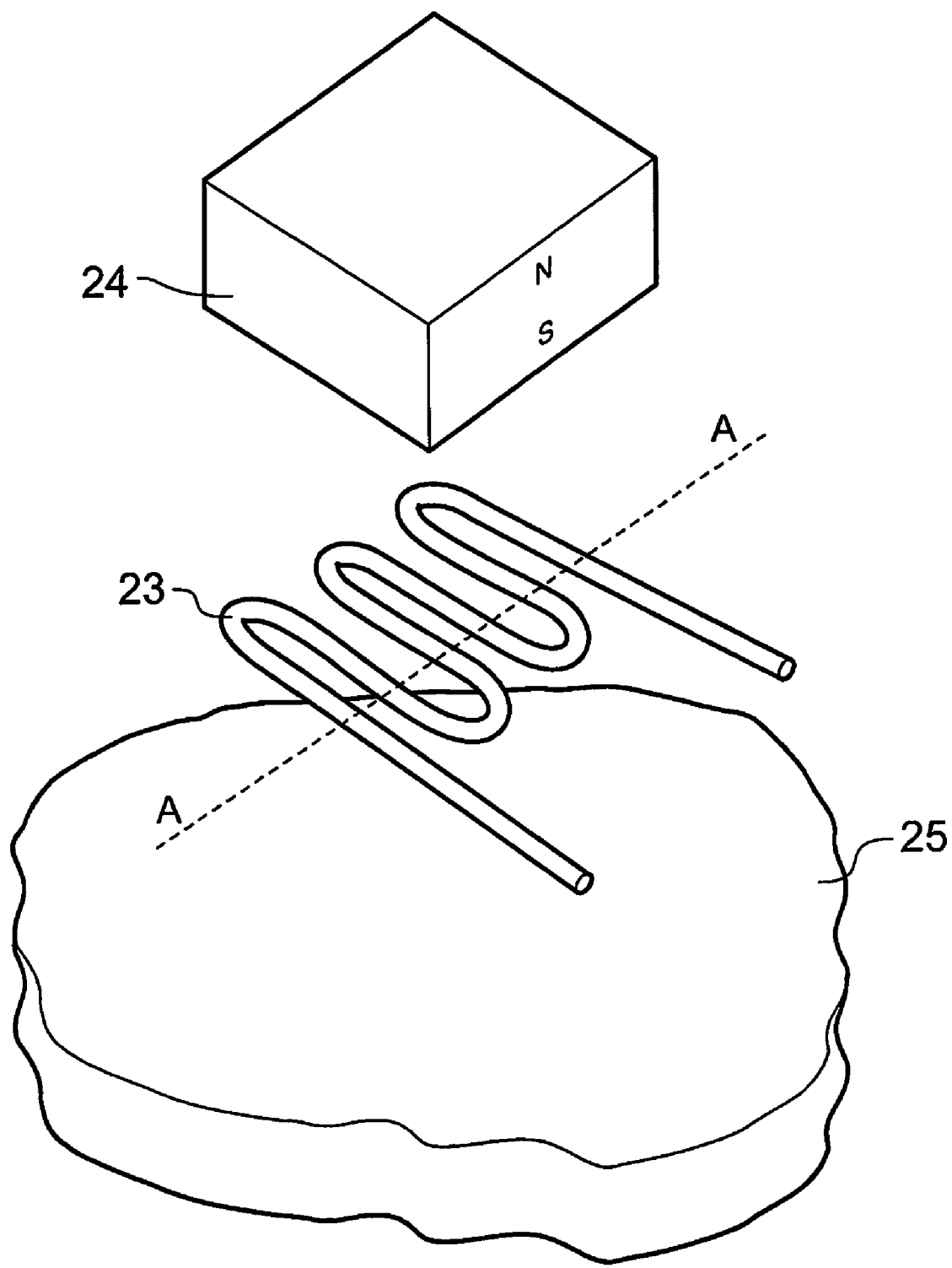
FIG. 8 shows part of another convention EMAT with no wear plate.
Figure 9:
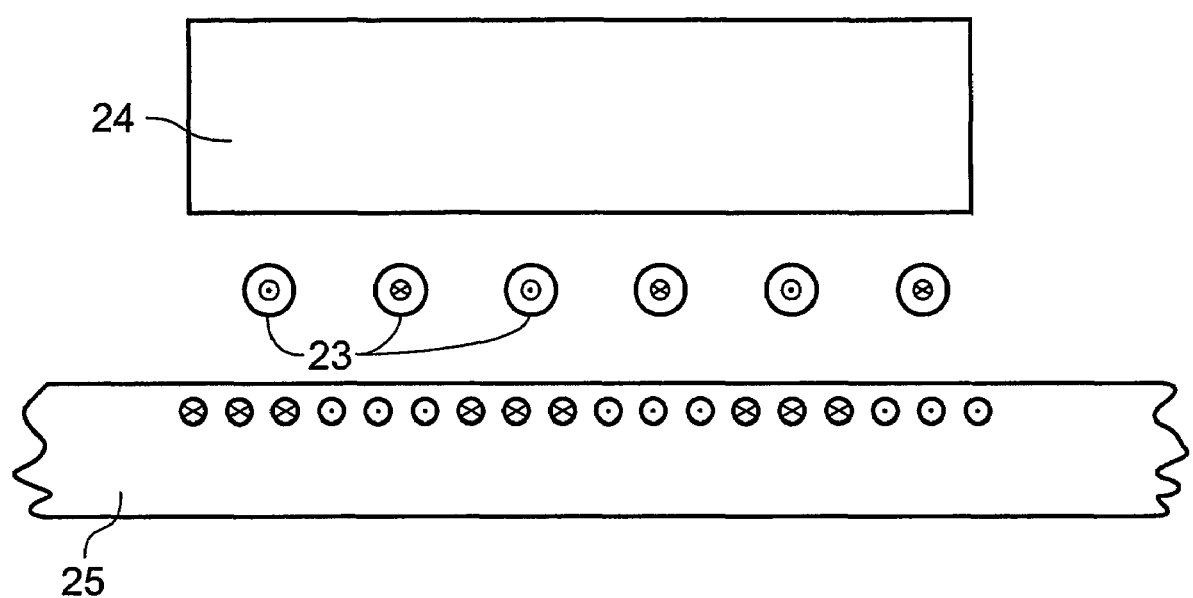
FIG. 9 is a vertical cross-section of the EMAT of FIG. 8, along the line A to A in FIG. 8.

By way of further example, a second embodiment of the invention will be described. In this example the EMAT and its wear plate generate in the test material acoustic waves in which the motion of the test material is predominantly orthogonal to both the test surface and the propagation direction. The resulting waves maybe of the Rayleigh, Lamb or vertically polarised shear type, depending on the geometry of the test material. The invention is not restricted to EMATS generating these wave types. FIGS. 8 and 9 show part of a conventional EMAT with no wear plate. The winding 23, is of the meander type and positioned under the pole of the single magnet 26, and over test material 25. The AC current flow in the meander coil 23 is illustrated in the conventional manner (dot and cross is a circle to represent current flowing respectively out of and into the plane of the paper. The image current flow in the test material is shown frozen in time and is distributed over the surface printing in the opposite direction to the flow in the nearest conductor of the meander coil. The current density in the test material varies smoothly changing from a maximum in one direction to a maximum in the opposite direction within a distance equal to the separation of the meander coil conductors. The smooth variation is approximately sinusoidal.

Figure 10:
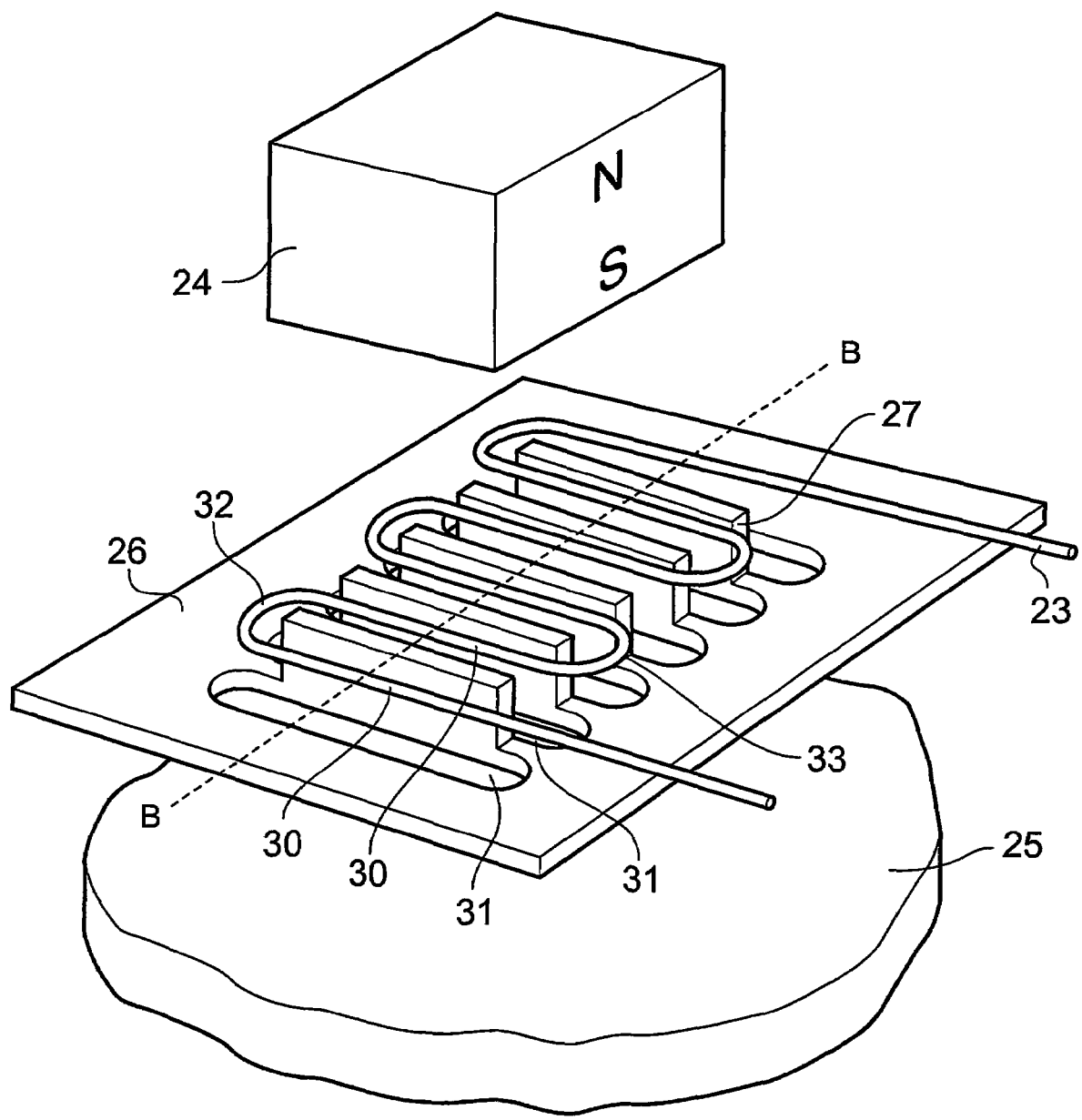
FIG. 10 shows an EMAT according to another embodiment of the invention, corresponding to FIG. 8 but having a wear plate.
Figure 11:
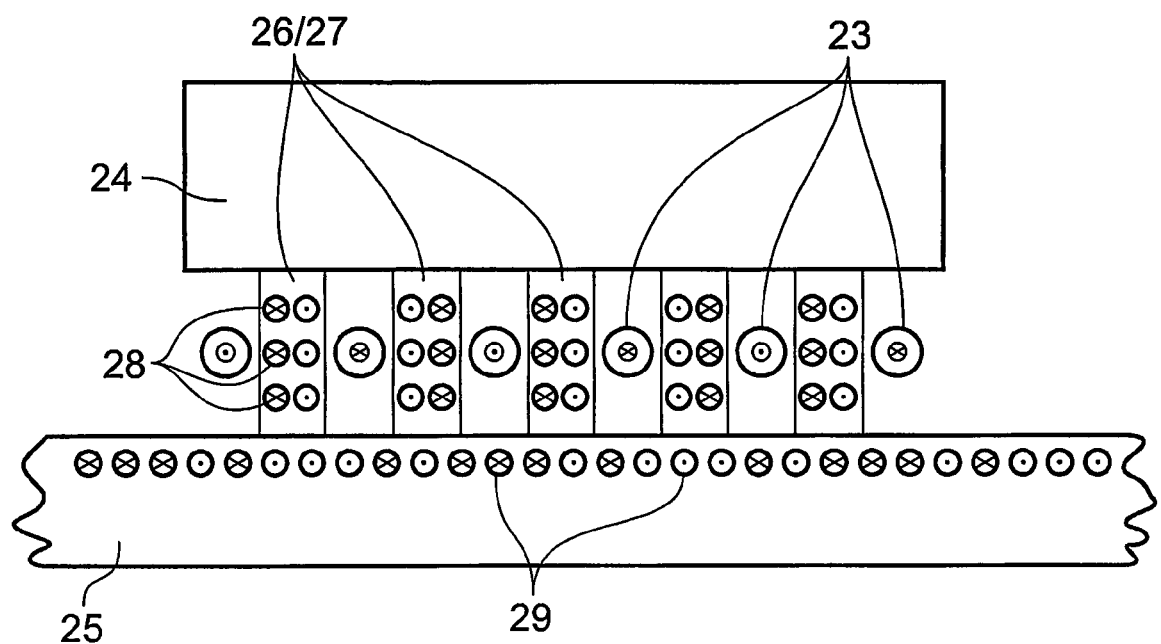
FIG. 11 shows a vertical cross-section of the EMAT of FIG. 10 along the line B to B in FIG. 10.

FIGS. 10 and 11 show an EMAT according to the second embodiment of the invention, which all the features of FIG. 8 are present, but in addition there is a slotted conductive and ferromagnetic wear plate 26. The meander coil windings are positioned above the open slots 31 of the wear plate 23. Thus, the meander coil 23 comprises a plurality of linear (straight) sections 30 which are aligned with the slots 31 in the wear plate 26, and which straight sections 30 are joined by 180° corners or meander 32. Thus, the wear plate 26 has one slot 31 for each straight section 30 of the meander coil 23. Moreover, as shown in FIG. 10, the wear plate may have projections or ligaments 27, of the same material as the wear plate 26, which project from the wear plate 26 to extend into the spaces between adjacent straight sections 30 of the meander coil 23.

The AC current in the meander coil 23, is shown frozen in time and is no different to the flow illustrated in FIG. 9. Since the metal ligaments of the wear plate 26/27 are electrically conductive, image currents 28, flow in the wear plate as illustrated. These image currents are themselves able to generate further image currents 29, in the test material. The image currents in the test material are therefore the result of current flows in the meander coil and also the image currents in the wear plate. The image currents in the test material are distributed across the surface of the test material fluctuating from a maximum in one direction to a maximum in the other direction over a distance equal to the winding separation of the meander coil. However, the test material image currents are significantly different to the original image currents shown in FIG. 9, where no wear plate is present. The most important difference is that the maximum AC current density in the test material, which occurs directly below any one linear section of the meander coil is increased compared to the case where no wear plate is present, all other geometric variables being the same. The wear plate can therefore enhance the AC image currents in the test material. Since the wear plate is also ferromagnetic it helps convey the DC magnetic flux from the magnet 24, to the test material with the effect that the overall acoustic performance of the EMAT is enhanced, compared to one in which no wear pate, according to the invention, is present.

By way of further explanation, the affect of a conductive or ferromagnetic wear layer on an EMAT is influenced by variation of the electrical and magnetic properties over the face area of the wear plate. The most easily controlled variation is produced by removal of material from specific areas of the wear plate, for example by cutting slots. The resulting electrical discontinuities across the wear face alter greatly the degree to which the high frequency magnetic field interacts with the test material. The associated magnetic permeability variations also influence the DC flux pattern imposed by the EMAT. Importantly, the joint action of the high frequency induced currents in the EMAT wear plate and the DC fields in the wear plate can play a novel role in enhancing the EMAT acoustic performance. By careful design, the wear plate can be arranged so that the EMAT performance is greatly increased compared to an EMAT with a conventional wear plate of similar thickness, subject to constraints due to the need for mechanical robustness. The material of the wear plate can then be selected to achieve greatly improved mechanical protection of the EMAT compared to a conventional wear material. The final design must also take into account the acoustic signals generated within the wear plate by EMAT action and any adverse affects caused by them.

AC Field Effects

The wear plate influences the EMAT performance in several ways. One of these is that it changes the AC fields and eddy currents within and around the EMAT and test material. Currents flowing within the wear plate are particularly important. The magnitude and surface area of high frequency eddy currents flowing adjacent the test material on the outer face of the wear plate are very significant and must be oriented correctly and maximized for best wear plate design.

To optimize the AC eddy currents within a horizontally polarised shear wave EMAT wear plate, slots should be cut into the wear plate transversely to the eddy current flow lines occurring on the inward facing (winding side) surface of the wear plate. The spacing of these slots and their lengths must ensure that current flows that remain on the inside surface of the wear plate, moving transversely to the slots, are forced to circulate by traveling down the slot walls and along the outer surface of the wear plate in the opposite direction to the flow on the inner surface. Any alternative current loops that circulate entirely within the inner surface plane of the wear plate, not reaching the outer surface, must be reduced where possible since these currents do not contribute to the acoustic performance of the EMAT and waste electrical energy.

An important means of reducing the wasteful AC currents circulating entirely within the inner surface plane particularly for a horizontally polarised shear ware EMAT is by extending the slots well beyond the most intense AC fields of the EMAT. This ensures that the eddy currents existing in the region beyond the slots, where they are more free to circulate within the inner plane, are weak and of little relevance to EMAT efficiency. An additional method of reducing AC currents at the inner surface is to decrease the distance between slots in regions close to the poles of the AC winding, where by definition AC flux has a significant component normal to the inner surface and the eddy currents prefer to circulate parallel to the inner plane.

The desired AC currents that flow on the outer surface of the wear plate behave like an additional electrical winding, which either complements or may dominate the effect of the main winding of the EMAT. Since these currents flow in a plane that is physically adjacent the test material, they induce stronger image currents in the test material than those produced directly by the main winding of the EMAT, which is more distant from the test material due to the presence of the wear plate. The performance of the EMAT is approximately proportional to the magnitude of the outer surface currents in the wear plate.

To ensure the desired circulation of currents, the wear plate electrical conductivity must be high and the wear plate thickness should be significantly larger than the electrical skin depth associated with the wear plate material at the operating frequency of the EMAT.

The AC current flows in the wear plate for any given winding arrangement, and overall plate dimensions can be optimized for acoustic effect by an appropriate design of slot pattern. However the slot pattern cannot be finalized without considering other factors, one being its impact on the DC field performance of the EMAT.

DC Field Effects

The performance of virtually all EMATs improves with increase in the DC field strength generated within the test sample. The DC field strength is affected by the slot distribution and is optimized by arranging at least some slots to coincide with boundaries of the DC magnetic pole faces on the front surface of the EMAT. With this arrangement, DC flux is forced to circulate by crossing the thickness of the wear plate and closing via the test specimen. Conversely the flux is prevented from travelling pole to pole within the wear plate since this would involve crossing a slot, which obstructs flux because it is a region of much reduced permeability.

Note that the DC field requirements can conflict with the mechanical integrity of the wear plate.

Mechanical Integrity

The DC rules for slot configuration cannot be implemented rigorously since the slots would then form closed loops as they trace out the boundary of the pole areas on the transducer face. This would divide the wear plate into disconnected parts and undermine the mechanical integrity of the plate. For example, in the case of a single magnet having one pole facing the test material, the slot would form a ring leaving a large central section of wear plate unsupported by the remaining plate and requiring the inconvenience of a separate means of support. A compromise on the ideal DC field design of the slots is therefore required in most practical cases.

Another factor influencing slot design is that a slot having an axis parallel to the intended travel direction of the EMAT may be preferential to a slot transverse to the travel direction under certain wear conditions. This is especially true if there are many closely spaced slots and the EMAT is likely to encounter objects that are capable of gouging the transducer face. The adverse consequence of having transverse closely spaced slots is that the thin ligaments of material between slots may become deformed due to the forces generated during gouging.

Acoustic Effects

The thickness and other dimensions of the wear plate influence the amplitude of acoustic waves caused by direct acoustic generation by the EMAT into the wear plate. These waves must be arranged so that they do not adversely affect the operation of the EMAT. Long-lasting reverberations within the wear plate that mask the reception of acoustic signals from the test material must be prevented.

The wear plate thickness may be one quarter the wavelength of the main wave mode excited within the wear plate. At this thickness the wear plate will not support normally-directed standing waves, which could resonate significantly after pulse transmission and create signals for which the EMAT would be particularly sensitive. Acoustic damping materials placed in contact with the wear plate are sometimes necessary to reduce the acoustic excitation of the wear plate. This requirement is less important where the EMAT is operating exclusively as a transmitter or exclusively as a receiver. Under these circumstances there can be no problem in which transmission pulse reverberation affects received signals (so called ring-down).

General

The wear plate slot arrangement should therefore take into account the AC field behaviour, the DC field behaviour and mechanical issues, namely the avoidance of partitioning the plate into isolated parts and giving due consideration to the travel direction of the EMAT and the damaging events that may occur. The wear plate thickness and general design should take into account the acoustic activity generated internally within the wear plate and its impact on EMAT acoustic performance. The material of the wear plate should have the necessary permeability and conductivity for satisfactory control of AC currents within the wear plate, and must be abrasion resistant.

A horizontally polarised shear wave EMAT having a wear plate constructed from 3 mm thick tool steel has achieved equivalent acoustic performance to a previous design in which the EMAT was protected by a 0.5 mm thick ceramic layer and which was proved to be insufficiently robust for pipeline inspection purposes.

Thus there is provided an EMAT the wear plate of which is of a ferromagnetic and electrically conductive material configured so as to have material discontinuities advantageous to the acoustic performance of the EMAT through its effect on both the DC and AC field components generated by the EMAT.

The invention claimed is:

1. An electromagnetic acoustic transducer for exciting ultrasound in a material under test, the transducer comprising magnetic means for applying a DC magnetic field to the material under test, an electrical coil supplied by an alternating current source for providing an AC magnetic flux within the material under test, and a wear plate adapted to engage with and slide along the surface of the material under test, characterised in that the wear plate comprises an electrically conductive, ferromagnetic material having apertures therein configured to provide electrical and magnetic discontinuity in the wear plate and to permit penetration of both the DC magnetic field and the AC magnetic flux into the material under test so as to create, by their interaction, ultrasonic vibration of the material under test.

2. A transducer according to claim 1, wherein the apertures comprise a plurality of parallel slots in the wear plate.

3. A transducer according to claim 1, wherein the magnetic means comprise a plurality of longitudinally aligned magnets adjacent ones of which have opposite poles abutting one another.

4. A transducer according to claim 3, wherein the apertures comprise a plurality of parallel slots in the wear plate and the slots are located below the boundaries between adjacent magnets.

5. A transducer according to claim 1, wherein the thickness of the wear plate is equal to one quarter of the wavelength of the main wave mode excited within the wear plate.

6. A transducer according to claim 1, wherein the magnetic means comprises at least one magnet and the electrical coil comprises a meander coil between the at least one magnet and the wear plate, the meander coil having a plurality of straight sections interconnected by meanders.

7. A transducer according to claim 6, wherein the plurality of straight sections of the meander coil are parallel.

8. A transducer according to claim 6, wherein the apertures comprise a plurality of parallel slots in the wear plate and wherein the straight sections of the meander coil are aligned with the slots in the wear plate.

9. A transducer according to claim 6, wherein the wear plate has a plurality of projections, each extruding between respective pair of adjacent straight sections of the meander coil.

10. A method of exciting ultrasound in a material under test, using an electromagnetic acoustic transducer, the method comprising:

applying a DC magnetic field to the material under test, providing an AC magnetic flux within the material under test, and causing a wear plate to engage with and slide along the material under test;

characterised in that:

the wear plate comprises an electrically conductive, ferromagnetic material having apertures therein which provide electrical and magnetic discontinuity in the wear plate;

whereby both the DC-magnetic field and the AC magnetic flux penetrate into the material under test, and ultrasonic vibration of the material under test occurs due to the interaction of the DC, magnetic field and AC magnetic flux.

11. A method according to claim 10, wherein the apertures comprise a plurality of parallel slots in the wear plate.

12. A method according to claim 11, wherein the slots extend substantially perpendicular to the direction of current flows in the material under test.

13. A method according to claim 10, wherein the thickness of the wear plate is equal to one quarter of the wavelength of the main wave mode excited within the wear plate.

14. A method according to claim 10, wherein the ultrasonic vibrations are horizontally polarised shear waves.

15. A method according to claim 10, wherein the DC magnetic field is applied by a magnetic means comprising at least one magnet and the AC magnetic flux is provided by an electrical winding comprising a meander coil between the at least one magnet of the magnetic means and the wear plate, the meander coil having a plurality of straight sections interconnected by meanders.

* * * * *